United States Patent [19]
Keller et al.

[11] Patent Number: 4,963,492
[45] Date of Patent: Oct. 16, 1990

[54] METHOD FOR THE ENZYMATIC RACEMATE RESOLUTION OF RACEMIC ALCOHOLS WITH/IN VINYL ESTERS BY TRANSESTERIFICATION

[75] Inventors: Reinhold Keller, Bad Soden am Taunus; Wolfgang Holla, Hofheim am Taunus; Gerd Fülling, Frankfurt am Main, all of Fed. Rep. of Germany

[73] Assignee: Hoechst Aktiengesellschaft, Frankfurt am Main, Fed. Rep. of Germany

[21] Appl. No.: 287,371

[22] Filed: Dec. 21, 1988

[30] Foreign Application Priority Data

Dec. 23, 1987 [DE] Fed. Rep. of Germany ....... 3743824

[51] Int. Cl.$^5$ ............................................. C12P 7/02
[52] U.S. Cl. .................................... 435/280; 435/155
[58] Field of Search ............................... 435/280, 155

[56] References Cited

U.S. PATENT DOCUMENTS 4,732,853  3/1988  Whitesides et al. ................ 435/280

FOREIGN PATENT DOCUMENTS 3624703  7/1986  Fed. Rep. of Germany .

OTHER PUBLICATIONS

M. Degueil-Castaing et al., "Enzymatic Reactions in Organic Synthesis: 2-Ester Interchange of Vinyl Esters," Tetrahedron Letters, vol. 28, No. 9, 1987, pp. 953-954.

A. Makita et al., "Lipase Catalyzed Synthesis of Macrocyclic Lactones in Organic Solvents," Tetrahedron Letters, vol. 28, No. 7, 1987, pp. 805-808.

Primary Examiner—Sam Rosen
Attorney, Agent, or Firm—Finnegan, Henderson, Farabow, Garrett, and Dunner

[57] ABSTRACT

Racemic alcohols can be resolved in good yield and with high enantiomeric purity in the presence of vinyl esters with the aid of lipases from pig pancreas, pig liver and microorganisms.

8 Claims, No Drawings

METHOD FOR THE ENZYMATIC RACEMATE RESOLUTION OF RACEMIC ALCOHOLS WITH/IN VINYL ESTERS BY TRANSESTERIFICATION

The invention relates to a method for the enzymatic racemate resolution of racemic alcohols with or in vinyl esters by transesterification, where the vinyl ester is cleaved to a ketone or an aldehyde and an "acid residue", and where the remaining acid residue forms an ester enantioselectively with an added racemic alcohol, and only one enantiomer of the alcohol remains unchanged. The ester and unreacted alcohol, and thus the two enantiomeric alcohols, can easily be separated from one another. The second enantiomer of the alcohol can, where appropriate, be obtained by cleavage of the ester.

Many optically active alcohols are important chiral precursors of biologically active substances (pharmaceuticals, natural substances, plant protection agents), and thus an economic method of preparation is of great importance. Examples of some pharmacological active substances whose preparation is facilitated with the method according to the invention are NSAIDs (nonsteroidal antiinflammatory drugs) such as ibuprofen and naproxen, beta-blockers such as nifenalol and penbutolol, bronchospasmolytics such as tolubuterol and bitolterol, and antimycotics such as tioconazole, pyrethroids such as allethrine, as well as tetramisole, tetrahydrozoline, (R)-(−)-tomoxetine and (S)-(+)-fluoxetine, and prostaglandins and carbohydrates.

It has been disclosed that vinyl esters can be transesterified under enzymatic catalysis with addition of alcohols in the presence of solvents such as tetrahydrofuran (M. Degueil-Castaing et al. Tetrahedron Letters, vol. 28, No. 9, pages 953–954, 1987). The enzyme which has been used is PPL (pig pancreatic lipase). No stereoselectivity was observed in the reaction. Atushi Makita et al. describe, in Tetrahedron Letters, vol. 28, No. 7, pages 805–808, 1987, the use of lipase P for the "lactonization" of ω-hydroxy carboxylic methyl esters in organic solvents such as cyclohexane, chloroform, hexane, heptane, benzene, toluene or dimethyl sulfoxide.

It has been proposed, in German Patent Application P No. 36 24 703.0, to prepare chiral compounds optically pure from prochiral diols by reaction with vinyl acetate in the presence of hydrolases. This takes place by selective esterification of only one of the two enantiotopic primary OH groups.

It has now been found, surprisingly, that racemic alcohols can be separated enzymatically by subjecting them to a selective enzyme-catalyzed transesterification reaction with vinyl esters, it being possible to dispense with solvents. Enzymes which can be used are lipases from pig liver and pig pancreas and from microorganisms such as Candida, Mucor, Rhizopus, Penicillium and, in particular, from Pseudomonas spec., such as lipase P and lipase FP (Amano, Japan).

This was all the more $urprising because it had hitherto been assumed that the liberated carbonyl compounds (aldehydes or ketones) react with the lipases and inactivate them.

Hence the invention relates to:
A method for the enzymatic racemate resolution of racemic alcohols, entailing a vinyl ester of the formula I

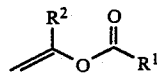

in which
R$^1$ denotes hydrogen, C$_1$–C$_{18}$-alkyl which is optionally substituted by halogen, or denotes phenyl or C$_1$–C$_3$-alkoxy-C$_1$–C$_4$-alkyl, and
R$_2$ denotes hydrogen or methyl, being reacted, in the presence of lipases from pig liver, pig pancreas and from microorganisms such as Candida, Mucor, Rhizopus, Penicillium, Aspergillus and Pseudomonas, with an alcohol of the formula II

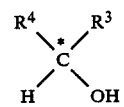

in which R$^3$ denotes C$_1$–C$_{18}$-alkyl or C$_4$–C$_{10}$-cycloalkyl, it also being possible for these radicals to be halogen-substituted,
and
R$^4$ denotes epoxy-C$_1$–C$_5$-alkyl, the epoxy group being in the β-position with respect to the OH group in the radical of the formula II,
R$^4$ denotes C$_1$–C$_{10}$-alkyl, C$_2$–C$_{10}$-alkenyl, C2-C10-alkynyl, C$_3$–C$_8$-cycloalkenyl, where the alkyl, alkenyl, alkynyl and cycloalkenyl radicals are optionally substituted by COOH, halogen, NO$_2$, CN, C$_1$–C$_4$-alkoxycarbonyl or phenyl, where the phenyl radical in turn can be substituted by halogen, NO$_2$, CN or C$_1$–C$_4$-alkoxy, or R$^4$ denotes aryl or heteroaryl, where the aryl or heteroaryl radicals are optionally substituted by C$_1$–C$_4$-alkyl, C$_1$–C$_4$-alkoxy, halogen, NO$_2$, CN or N Pg, where Pg represents an amino protective group,
or in which
R$^3$ and R$^4$ together represent an alkylene or alkenylene radical of the formula IIIa,b

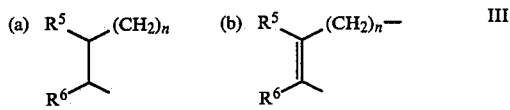

in which
n$_5$ is 1, 2 or 3, and
R$^5$ and R$^6$ are identical or different and denote hydrogen, C$_2$–C$_4$-alkenyl or C$_1$–C$_4$-alkyl, or
R$^5$ and R$^6$ together denote fused-on phenyl or fused-on naphthyl, where the phenyl or naphthyl radical is optionally substituted by C$_1$–C$_4$-alkyl, C$_1$–C$_4$-alkoxy, NO$_2$, CN or halogen,
and where a methylene unit in the alkenylene chain can also be replaced by a carbonyl group, and subsequently isolating the resulting optically pure alcohol of the formula II and, where appropriate, obtaining the other enantiomer from the remaining ester.

Halogens are to be understood to comprise fluorine, chlorine, bromine and iodine, especially chlorine and bromine. "Aryl" is to be understood to comprise, for example, phenyl, naphthyl, phenanthryl, anthryl and fluorenyl, especially phenyl, naphthyl and phenanthryl. "Heteroaryl" is to be understood to comprise, for example, furyl, thienyl, pyrrolyl, pyridyl, pyrimidyl, pyrazinyl, imidazolyl, oxazolyl, thiazolyl and indolyl, especially furyl, thienyl, pyrrolyl and pyridyl. The amino protective group "Pg" is to be understood to comprise the amino protective groups customarily used in peptide chemistry, for example benzyloxycarbonyl (Cbz=Z), benzoyl, benzyl, butyloxycarbonyl (Boc), 9-fluorenylmethoxycarbonyl (Fmoc), benzhydryl, allyloxycarbonyl (Aloc), tosyl, methoxymethyl (MOM), tetrahydropyranyl (THP), acetyl as well as alkyl or cycloalkyl groups such as, for example, N-methyl, N,N-dimethyl or piperidine or morpholine. "Fused-on phenyl" or "fused-on naphthyl" is to be understood to comprise a phenyl or naphthyl radical in which the C—C double bond of the radical of the formula III forms part of the phenyl or naphthyl radical. The optionally substituted radicals $R^1$, $R^3$, $R^4$, $R^5$ and $R^6$ are preferably monosubstituted.

Alkyl and alkenyl radicals having 3 and more carbon atoms, and alkynyl radicals having 4 and more carbon atoms, can be both straight-chain and branched. It is particularly preferable to use as racemic alcohol of the formula II one of the compounds listed in Table 1.

The method according to the invention has the following advantages over conventional methods for the racemate resolution of alcohols:

(a) at least one enantiomer is always highly (optically) pure, and in fact usually both are;
(b) it is easy to recover the enzyme which is used;
(c) it is very straightforward to separate the "alcohol" from the "ester" produced in the resolution; in the ideal case the two can be separated by distillation;
(d) additional solvent dispensed with;
(e) high and rapid conversion with use of comparatively small amounts of enzyme.

In the method according to the invention, the vinyl ester of the formula I is cleaved to carboxylic acid and the appropriate vinyl alcohol. The vinyl alcohol immediately rearranges to a ketone or an aldehyde. Thus, a reverse reaction is completely suppressed. Under the catalytic action of the said lipases, in this way there is rapid and selective esterification, in high yields, of one enantiomer from the racemic alcohol, and the other enantiomer remains unchanged in the reaction mixture.

The method according to the invention is particularly suitable for resolving those alcohols which have in the $\beta$-position with respect to the OH group a C—C double or triple bond, or which have in this position an epoxide or a double-bond equivalent such as a $C_3$ ring.

The best procedure for the method according to the invention is to make a solution of the vinyl ester of the formula I, preferably vinyl acetate or vinyl chloroacetate, and to add both the enzyme and the alcohol which is to be resolved. The enzyme which is preferably used is a lipoprotein lipase from Pseudomonas spec., especially lipase P or lipase FP, which are commercially available (Amano Pharmaceuticals, Nagoya, Japan). Furthermore, the enzyme can also be used in immobilized form, suitable for this being all conventional immobilization methods and supports. Immobilized enzyme and free enzyme can also be used in a column method. The amount of enzyme is chosen freely depending on the size of the batch, on the reactivity of the alcohol, on the desired reaction time and on the nature of the enzyme (free or immobilized) and can easily be determined in the individual case by simple preliminary experiments. The alcohol to be resolved is used in concentrations of 1% to 200%, preferably of 10% to 40%, based on the volume of the vinyl or methylvinyl ester used. It is even possible in some cases to employ vinyl esters only in stoichiometric amounts relative to one enantiomer.

The reaction temperature is $-10°$ C. to $100°$ C., preferably $15°$ C. to $50°$ C. It is expedient to stir the solution during the reaction. The reaction times vary with the racemic alcohol used, and depending on the amount of enzyme, between a few hours and up to 4 weeks; however, in the majority of cases they are between 3 hours and 3 days.

The methyl or methylvinyl esters of the formula I which cannot be bought can be prepared in a straightforward manner, for example by transesterification of vinyl acetate with the appropriate carboxylic acids.

The racemic alcohols of the formula II which cannot be bought are obtained, for example, by reduction from the corresponding ketones, most of which can be bought, or by $\alpha$-bromination of corresponding ketones with subsequent reduction to the alcohol. Other alcohols or ketones which cannot be bought can be prepared straightforwardly by methods known from the literature, for example by Grignard or other conventional addition reactions.

The products resulting in the method according to the invention, acetaldehyde or acetone, carboxylic ester and alcohol, can be separated in a known manner. In the ideal case, the unreacted alcohol is obtained by separation by distillation. If separation by distillation is impossible, the separation is carried out by chromatography or by extraction or crystallization. One possibility of increasing the boiling point difference between the enzymatically formed lower ester and the unreacted alcohol is to use, in place of a vinyl ester, the corresponding $\alpha$-halogenocarboxylic vinyl ester (for example vinyl chloroacetate).

If the other enantiomer is also to be prepared pure, then the ester is initially isolated and then cleaved to the acid and alcohol in a known manner.

Obtained in this way are alcohols with enantiomeric purities exceeding 95% (ee value).

The enzyme used for the reactions can easily be recovered by filtration.

The invention is explained in detail in the examples which follow.

EXAMPLE

General procedure

The racemic alcohol is dissolved or suspended in the vinyl ester. To this is added lipase P (or lipase FP) in free or immobilized form, and the mixture is stirred at the temperature indicated in Table 1. After the reaction is complete, the enzyme is removed by filtration (both the free and the immobilized enzyme are re-usable), the remaining solution is evaporated to dryness in vacuo, and the alcohol/ester mixture remaining as residue is separated by column chromatography on silica gel or by extraction, crystallization or distillation. Table 1 indicates the resulting products, the variable parameters of the method (amount of enzyme, amount of alcohol, amounts of vinyl ester, reaction temperature, reaction time) and the product characteristics and chemical yield.

| Ex. No. | racem. alcohol | Amount of alcohol | Amount of enzyme | Amount + type of vinyl ester | Reaction temperature | Reaction time | Alcohol ee | Alcohol $\alpha_D^{(a)}$ | Alcohol chem. yield | Ester ee | Ester $\alpha_D^{(a)}$ | Ester chem. yield |
|---|---|---|---|---|---|---|---|---|---|---|---|---|
| 1 |  | 1.00 g | 100 mg | 5 ml, VA | RT | 15.5 h | >95% | −28 CHCl₃ 40% | 93% | + CHCl₃ | +42% | 42% |
| 2 | 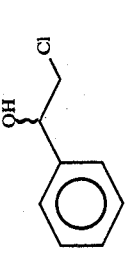 | 1.00 g | 100 mg | 10 ml, VA | RT | 7 d | 75% | −38 | 40% | >95% | +74 Acetone | 48% |
| 3 | 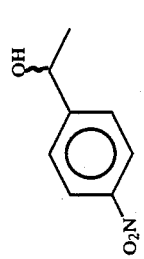 | 1.00 g | 100 mg | 5 ml, VA | RT | 48 h | >95% | −31 EtOH | 40% | >95% | +80 EtOH | 43% |
| 4 | 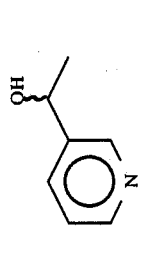 | 1.00 g | 100 mg | 10 ml, VA | RT | 65 h | >95% | — | 38% | 90% | — | 42% |
| 5 | 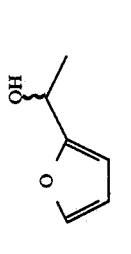 | 1.00 g | 100 mg | 5 ml, VA | RT | 17 h | >95% | −21 EtOH | 35% | ≧88% | −154 EtOH | 40% |
| 6 | 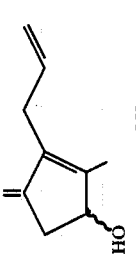 | 1.00 g | 100 mg | 15 ml, VA | RT | 18 h | >95% | +14.8 CHCl₃ | 47% | 90% | −29.12 CHCl₃ | 44% |
| 7 | 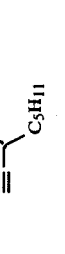 | 1.00 g | 100 mg | 5 ml, VA | RT | 29 h | >23% | — | n.d. | 55% | — | 25% |

-continued

| Ex. No. | racem. alcohol | Amount of alcohol | Amount of enzyme | Amount + type of vinyl ester | Reaction temperature | Reaction time | Alcohol ee | Alcohol $\alpha_D^{(a)}$ | Alcohol chem. yield | Ester ee | Ester $\alpha_D^{(a)}$ | Ester chem. yield |
|---|---|---|---|---|---|---|---|---|---|---|---|---|
| 8 | 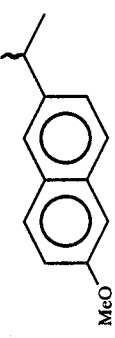 | 2.5 g | 2.5 g | 250 ml, VA | RT | 7 d | ≧95% | −47.8 CHCl$_3$ | 28% | 94% | +122.7 CHCl$_3$ | 32% |
| 9 | 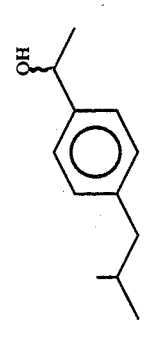 | 5 g | 0.5 g | 50 ml, VA | RT | 30 h | ≧95% | −41.6 CHCl$_3$ | 42% | ≧95% | +97.6 CHCl$_3$ | 33% |
| 10 | 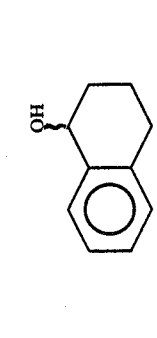 | 1 g | 0.1 g | 5 ml, VA | RT | 76 h | ≧97% | +31.6 CHCl$_3$ | 36% | 76% | +81.4 CHCl$_3$ | 43% |
| 11 | 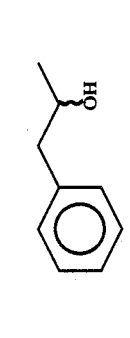 | 1.00 g | 0.1 g | 5 ml, VA | RT | 4 d | 84% | +32.0 CHCl$_3$ | 44% | ≧95% | −8.5 CHCl$_3$ | 38% |
| 12 | 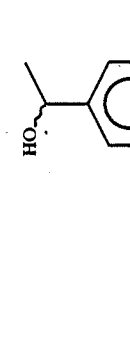 | 160 mg | 20 mg | 2 ml, VA | RT | 44 h | 75% | −29.6 CHCl$_3$ | n.d. | ≧95% | +95.0 CHCl$_3$ | n.d. |
| 13 | 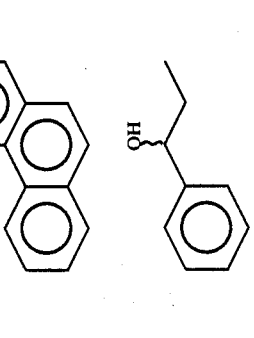 | 1.00 g | 0.1 g | 5 ml, VA | RT | 4 d | 56% | −28.4 CHCl$_3$ | n.d. | ≧95% | +103.4 CHCl$_3$ | n.d. |

-continued

| Ex. No. | racem. alcohol | Amount of alcohol | Amount of enzyme | Amount + type of vinyl ester | Reaction temperature | Reaction time | Alcohol | | | Ester | | |
|---|---|---|---|---|---|---|---|---|---|---|---|---|
| | | | | | | | ee | $\alpha_D^{(a)}$ | chem. yield | ee | $\alpha_D^{(a)}$ | chem. yield |
| 14 | OH, cyclopropyl-phenyl methanol | 1.00 g | 0.1 g (+0.4 g) | 10 ml, VA | RT | 13 (+2) d | 46% | — | n.d. | ≧95% | — | n.d. |
| 15 | OH, 1-phenyl-2-methylpropanol | 6.1 g | 0.2 g | 17.2 ml, VA | RT | 6 h | ≧98% | −44.0 | 40% | ≧98% | +104.2 | 45% |
| 16 | OH, 1-phenyl-2-methylpropanol | 6.1 g | 0.2 g | 2.15 ml, VA | RT | 6 h | ≧98% | −43.5 | 41% | ≧98% | +104.2 | 45% |
| 17 | ″ | 6.1 g | 0.2 g | 17.2 ml, VA | 82° C. | 3 h | ≧98% | −44.1 | 44% | ≧98% | +102.8 | 42% |
| 18 | ″ | 6.1 g | 0.2 g | 20 ml, VCA | RT | 5 h | ≧97% | −43.0 | 39% | ≧95% | +100.4 | 40% |
| 19 | ″ | 6.1 g | 5 g[b] | 17.2 ml, VA | RT | 7 h. | ≧98% | −44.1 | 39% | ≧98% | +104.2 | 42% |
| 20 | oct-1-en-3-ol | 52 g | 3 g | 150 ml, VA | RT | 24 h | >86% | −8.7 | 38% | >84% | −5.0 | 46% |
| 21 | OH, 1-(4-nitrophenyl)-2-bromoethanol | 4.7 g | 4.7 g | 50 ml, VA | RT | 3 d | ≧95% | −28.3 | 40% | ≧95% | +49.3 | 45% |
| 22 | OH, 1-phenyl-3-chloropropanol | 1.0 g | 1.0 g | 10 ml, VA | RT | 7 d | ≧87% | −22.2 | n.d. | 77% | +42.9 | n.d. |

-continued
| Ex. No. | racem. alcohol | Amount of alcohol | Amount of enzyme | Amount + type of vinyl ester | Reaction temperature | Reaction time | Alcohol ee | Alcohol $\alpha_D^{(a)}$ | Alcohol chem. yield | Ester ee | Ester $\alpha_D^{(a)}$ | Ester chem. yield |
|---|---|---|---|---|---|---|---|---|---|---|---|---|
| 23 | 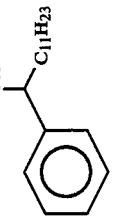 | 0.5 g | 0.5 g | 5 ml, VA | RT | 10 d | 54% | n.d. | n.d. | ≧88% | n.d. | n.d. |
| 24 | 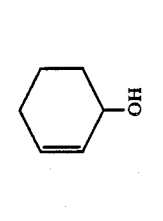 | 1.0 g | 0.1 g | 10 ml, VA | RT | 6 h | 31% | −34 | n.d. | 17% | +37 | n.d. |
| 25 | 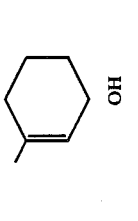 | 2.0 g | 0.2 g | 10 ml, VA | RT | 1 d | ≧88% | −85.0 | 25% | 54% | +61.3 | 67% |
| 26 | 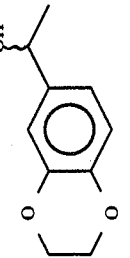 | 1.0 g | 0.01 g | 5 ml, VA | RT | 18 h | 85% | n.d. | 37% | ≧95% | +74.0 | 45% |
| 27 | 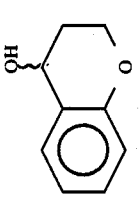 | 1.0 g | 0.01 g | 5 ml, VA | RT | 16 h | ≧95% | −72.0 | 40% | ≧86% | +172.5 | 45% |
| 28 | 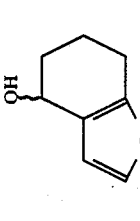 | 0.5 g | 0.3 g | 2.5 ml, VA | RT | 23 h | ≧95% | +2.6 | 29% | 70 | +101.0 | 54% |

-continued

| Ex. No. | racem. alcohol | Amount of alcohol | Amount of enzyme | Amount + type of vinyl ester | Reaction temperature | Reaction time | Alcohol ee | Alcohol $\alpha_D^{(a)}$ | Alcohol chem. yield | Ester ee | Ester $\alpha_D^{(a)}$ | Ester chem. yield |
|---|---|---|---|---|---|---|---|---|---|---|---|---|
| 29 | (1-(thiophen-2-yl)ethanol) | 1.0 g | 0.02 g | 5 ml, VA | RT | 5 h | 80 | −18.4 | 48% | 92 | +142.0 | 42% |
| 30 | (1-(5-chlorothiophen-2-yl)ethanol) | 1.0 g | 0.25 g | 5 ml, VA | RT | 11.5 h | 54% | −35.5 | 90% | 92% | +16.5 | 40% |
| 31 | (1-(thiazol-2-yl)ethanol) | 0.3 g | 0.3 g | 2 ml, VA | RT | 48 h | 48% | −9.0 | 63% | ≧95% | +75.0 | 31% |

(a) ee determination based on $^1$H NMR using chiral shift reagents
(b) lipase P immobilized on silica gel; VA = vinyl acetate; VCA = vinyl chloroacetate
n.d. = not determined;
RT = room temperature

We claim:
1. A method for the enzymatic racemate resolution of a racemic alcohol, which comprises a vinyl ester of the formula I

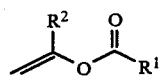

in which
R$^1$ denotes C$_1$–C$_{18}$-alkyl which is unsubstituted or halogen-substituted, phenyl or C$_1$–C$_3$-alkoxy-C$_1$–C$_4$-alkyl, and
R$^2$ denotes hydrogen or methyl,
being reacted, in the presence of a lipase from pig liver, pig pancreas or from a microorganism selected from Candida, Mucor, Rhizopus, Penicillium, Aspergillus and Pseuudomonas, with a racemic alcohol of the formula II

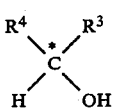

in which
R$^3$ denotes C$_1$–C$_{18}$-alkyl or C$_3$–C$_{10}$-cycloalkyl, each being unsubstituted or halogen-substituted, and
R$^4$ denotes epoxy-C$_1$–C$_5$-alkyl, the epoxy group being in the β-position with respect to the OH group in the radical of the formula II,
or
R$^4$ denotes C$_1$–C$_{10}$-alkyl, C$_2$–C$_{10}$-alkenyl, C$_2$–C$_{10}$-alkynyl, C$_3$–C$_8$-cycloalkenyl, where the alkyl, alkenyl, alkynyl and cycloalkenyl radicals are unsubstituted or substituted by COOH, halogen, NO$_2$, CN, C$_1$–C$_4$-alkoxycarbonyl or phenyl, where the phenyl radical in turn is unsubstituted or substituted by halogen, NO$_2$, CN or C$_1$–C$_4$-alkoxy, or
R$^4$ denotes aryl or heteroaryl, where the aryl or heteroaryl radicals are unsubstituted or substituted by C$_1$–C$_4$-alkyl, C$_1$–C$_4$-alkoxy, halogen, NO$_2$, CN or N Pg, where Pg represents an amino protective group,
or in which
R$^3$ and R$^4$ together represent an alkenylene radical of the formula III (a) or (b)

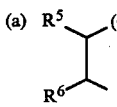 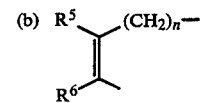

n is 1, 2 or 3, and
R$^5$ and R$^6$ are identical or different and denote hydrogen, C$_2$–C$_4$-alkenyl or C$_1$–C$_4$-alkyl, or
R$^5$ and R$^6$ together denote fused-on phenyl or fused-on naphthyl, where the phenyl or naphthyl radical is unsubstituted or substituted by C$_1$–C$_4$-alkyl, C$_1$–C$_4$-alkoxy, NO$_2$, CN or halogen,
and where the alkenylene radical of the formula III can also have a keto group,
and subsequently isolating the resulting optically pure racemic alcohol of the formula II.

2. The method as claimed in calim 1, wherein at least oen of the following conditions is met:
R$^1$ denotes C$_1$–C$_4$-alkyl which is unsubstituted or chlorine-substituted;
R$^3$ denotes C$_1$–C$_7$-alkyl which is unsubstituted or chlorine-substituted, R$^3$ denotes C$_3$–C$_5$-cycloalkyl;
R$^4$ denotes C$_1$–C$_4$-alkyl, C$_2$–C$_4$-alkenyl or C$_2$–C$_4$-alkynyl, where the alkyl, alkenyl or alkynyl radicals are unsubstituted or phenyl-substituted, or
R$^4$ denotes phenyl, naphthyl, phenanthryl, furyl, thienyl, pyrrolyl or pyridyl, where these radicals in turn are unsubstituted or substituted by halogen, NO$_2$, CN, C$_1$–C$_4$-alkyl or C$_1$–C$_4$-alkoxy, and
R$^5$ and R$^6$ together form fused-on phenyl.

3. The method as claimed in claim 1, wherein at least one of the following conditions is met:
R$^1$ denotes methyl or chloromethyl,
R$^3$ denotes C$_1$–C$_5$-alkyl which is. unsubstituted or chlorine-substituted, R$^3$ denotes cyclopropyl, and
R$^4$ denotes phenyl, naphthyl, phenanthryl, furyl or pyridyl, where these radicals in turn are unsubstituted or substituted by NO$_2$ or methoxy.

4. The method as claimed in claim 1, wherein lipase from Pseudomonas is used.

5. The method as claimed in calim 1, wherein after isolating the racemic alcohol of the formula II, obtaining the other enantiomer from the remaining ester.

6. A method for the enzymatic racemate resolution of a racemic alcohol which comprises a vinyl ester of the formula I

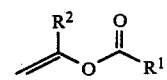

R$^1$ denotes C$_1$–C$_{18}$-alkyl which is unsubstituted or halogen-substituted, phenyl or C$_1$–C$_3$-alkoxy-C$_1$–C$_4$-alkyl, and
R$^2$ denotes hydrogen or methyl,
being reacted, in the presence of a lipase from pig liver, pig pancreas or from a microorganism selected from Candida, Mucor, Rhizopus, Penicillium, Aspergillus and Psuedomonas, with a racemic alcohol of the formula 26, 27 or 28

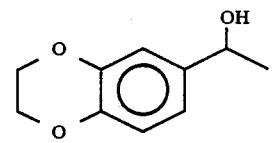

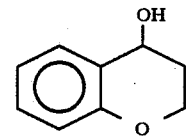

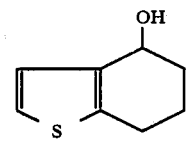

and subsequently isolating the resulting optically pure racemic alcohol of the formula 26, 27 or 28.

7. The method as claimed in alim 6, wherein after isolating the racemic alcohol of the formula II, obtaining the other enantiomer from the remaining ester.

8. The method as claimed in claim 6, wherein lipase from Pseudomonas is used.

* * * * *